US006455261B1

(12) United States Patent
Wong et al.

(10) Patent No.: US 6,455,261 B1
(45) Date of Patent: Sep. 24, 2002

(54) DIAGNOSTIC ASSAY USING MICROPEROXIDASE

(76) Inventors: Sie-Ting Wong, 15 N. French Ct., Mundelein, IL (US) 60060; Sung-Chul Lee, 510 Roosevelt Dr., Libertyville, IL (US) 60048

( * ) Notice: Subject to any disclaimer, the term of this patent is extended or adjusted under 35 U.S.C. 154(b) by 0 days.

(21) Appl. No.: 07/511,878

(22) Filed: Apr. 20, 1990

Related U.S. Application Data

(63) Continuation of application No. 07/227,448, filed on Aug. 2, 1988, now abandoned, which is a continuation of application No. 06/713,514, filed on Mar. 19, 1985, now abandoned.

(51) Int. Cl.$^7$ .............................................. G01N 33/53
(52) U.S. Cl. ...................... 435/7.1; 435/7.9; 435/7.91; 435/10
(58) Field of Search ................ 435/7.1, 7.9, 7.91, 435/10, 25, 28

(56) References Cited

U.S. PATENT DOCUMENTS

| | | | | | |
|---|---|---|---|---|---|
| 4,269,938 A | * | 5/1981 | Frank | ........................... | 435/28 |
| 4,273,874 A | * | 6/1981 | Nakanishi | .................... | 435/10 |
| 4,289,747 A | * | 9/1981 | Chu | ............................... | 435/7 |
| 4,334,069 A | * | 6/1982 | Bucker et al. | ............... | 544/237 |
| 4,384,042 A | * | 5/1983 | Miike | ........................... | 435/10 |
| 4,414,326 A | * | 11/1983 | Goldberg | ..................... | 435/28 |
| 4,447,542 A | * | 5/1984 | Gantzer | ........................ | 435/28 |
| 4,455,371 A | * | 6/1984 | Richardson | .................. | 435/28 |
| 4,626,501 A | * | 12/1986 | Landes | ........................ | 544/264 |
| 4,689,309 A | * | 8/1987 | Jones | .......................... | 435/805 |
| 4,999,285 A | * | 3/1991 | Stiso | ........................... | 435/7.9 |

FOREIGN PATENT DOCUMENTS

| EP | 0138357 | 4/1985 |
|---|---|---|
| EP | 0158964 | 10/1985 |
| JP | 109200 | 6/1984 |

OTHER PUBLICATIONS

Tu, At, et al., *Experimentia*, vol. 24, No. 3, pp 219–221, 1968.*
*Principles of Enzymatic Analysis*, Bergmeyer, ed. Verlag Chemie, Weinheim, 1978, pp. 56–78.*
Stott et al. Chemical Abstracts 102: 217657d (1984).*
Tiggermann et al J. Histochemistry and Cytochemistry 29(12) p 1387–1396 (1981).*
Bockelbank, et al., Biological Abstracts, vol. 78, Abstract 78074805, 1984.
Kim, et al., Clin. Chem., vol. 28/5, pp. 1120–1124, 1982.
Klingler, et al., Steroids, vol. 42, No. 2, pp. 123–136, 1983.
Koehn, et al., Steroids, vol. 36, No. 4, pp. 421–437, 1980.
David A. Baldwin, et al, "Mechanism of activation of $H_2O_2$ by peroxidases: kinetic studies on a model system", FEBS 2470, vol. 183, No. 2, Apr. 1985.
Bo Olsson, *Anal. Chim. Acta*, 136, p. 113–119 (1982).
H. R. Schroeder, et al. *Anal. Chem.*, 50 (8) p. 1114–1120 (1978).
F. Kohen, et al., *Steroids*, 38 (1), p. 73–88 (1981).

* cited by examiner

*Primary Examiner*—Sheela Huff
(74) *Attorney, Agent, or Firm*—Richard D. Schmidt; Matthew R. Hooper; David J. Schodin

(57) ABSTRACT

A method for determining the presence and/or the amount of an analyte in a sample which method comprises contacting the sample containing the analyte with a peroxidatively-active material to produce a peroxide, a substance capable of producing a detectable response in the presence of the peroxide as a measure of the analyte present in the sample, and a microperoxidase catalyst.

7 Claims, No Drawings

DIAGNOSTIC ASSAY USING MICROPEROXIDASE

This is a continuation of U.S. Ser. No. 07/227,448 filed on Aug. 2, 1988, now abandoned, which is a continuation of U.S. Ser. No. 06/713,514 filed on Mar. 19, 1985, now abandoned.

BACKGROUND OF THE INVENTION

1. Field of the Invention

This invention relates to diagnostic assays, and more particularly to diagnostic assays which utilize peroxides and wherein a microperoxidase is utilized advantageously, in place of an enzyme, as a reagent.

2. Background Art

The use of enzymes as reagents is now widely recognized, especially in clinical determinations of the presence and/or concentration of a variety of analytes of interest and clinical significance in biological fluids, for example, blood serum, plasma, whole blood, urine, spinal and amniotic fluids. As used herein, an "enzyme" is defined as a polypeptide having a molecular weight greater than about 10,000 daltons and exhibiting catalytic activity. In general, two basic approaches have been used in the art with respect to such enzymatic assays. In one, a precursor or substrate of clinical importance is converted by an enzyme into detectable compounds, or signals, such as color or fluorescence, which are detectable. In the second, the enzyme itself is coupled with an analyte and the enzyme activity is determined as a measure of the analyte present. Whichever approach is utilized, however, the enzyme reagent is generally required to possess good stability, be readily commercially available, and as well have what is termed in the art a "high turnover number". In addition, it is desirable that the enzyme be active with respect to substrates which are readily commercially available, relatively stable and inexpensive and which produce easily detectable products or signals.

Typical of enzymes commonly used in assays such as the aforedescribed are redox enzymes, kinases and esterases. One example of the conventional use of enzymes in clinical chemistry assays is in the determination of uric acid, a procedure which has typically employed horseradish peroxidase (HRPO). In that analysis, uric acid is determined using HRPO in conjunction with uricase enzymes. Typical clinical test samples contain uric acid in concentrations less than about 12 milligrams per deciliter (mg/dl), and are contacted in such assays with microbial uricase which converts the uric acid to allantoin and hydrogen peroxide. The hydrogen peroxide thus formed is used to oxidize chromogenic substrates catalyzed by the HRPO, which substrates develop color as a measure of the presence and/or concentration of uric acid in the sample. The color development can then be measured visually, spectrophotometrically or by other instrumental means, and its intensity correlated with the amount of uric acid in the sample.

However, the use of HRPO or other enzymes in such conventional assays is not without problems. For example, the pH values for optimum activity of enzymes such as HRPO and uricase are quite different, and thus neither can be utilized efficiently in such assays. Because uricase is an expensive enzyme, the reaction conditions of such assays ordinarily have been adjusted to facilitate the most efficient use of uricase; such adjustment, in turn, requires concomitant use of a high concentration of HRPO to achieve a rapid kinetic response. In addition, HRPO is known to lose activity in storage, and hence has a limited shelf life.

Another conventional use of HRPO is as an enzyme label in immunoassays. For example, a number of known enzyme immunoassays involve contacting samples suspected of containing antigens of interest with a solid phase support containing or coated with an immobilized, adsorbed or covalently coupled specific antibody to the antigen. After incubation and washing of the solid phase, a conjugate, which comprises a specific antibody to the antigen which has been labeled with HRPO, is added and incubated with the solid phase. The solid phase is again washed, and the activity of the HRPO which becomes bound to the solid phase with the conjugate is then determined, usually by spectrophotometric means, by addition of an indicator substance comprising a chromogenic or other substrate. Upon contact with the HRPO, the indicator, if a chromogen, produces a color detectable by the spectrophotometer. The spectrophotometric reading can then be correlated with similar readings taken from known concentrations of the antigen, thereby to determine the concentration of antigen in the sample.

Horseradish peroxidase can also be disadvantageous in enzyme immunoassays of the type aforedescribed. For example, coupling conditions, well-known in the art, which ordinarily are used to produce the antibody-HRPO conjugate, have a tendency to inactivate both the antibody and the HRPO. Moreover, such coupling conditions usually tend to produce a heterogeneous product requiring extensive purification and careful optimization for each particular assay. Also, the conjugates produced have a marked tendency to become unstable during storage, limiting their shelf-life.

SUMMARY OF THE INVENTION

In accordance with the present invention, a method has been discovered for carrying out diagnostic assays which overcomes the aforedescribed disadvantages of conventionally-used enzymes. The method can be employed to particular advantage in determining various analytes in biological fluids, such as blood serum, whole blood, plasma, urine, spinal and amniotic fluids, and the like. The method utilizes a microperoxidase as a non-enzymatic catalyst, to provide such assays with advantageous stability and the capability of being used efficiently with enzymes to provide rapid kinetic responses to analytes.

In a preferred embodiment, the method which is improved by the invention comprises contacting a sample containing an analyte, or a derivative thereof, which is of interest with an oxidoreductase enzyme to produce a peroxide reaction product; the reaction product, in the presence of a peroxidease and a substance capable of producing a detectable response thereto, can then be determined as a measure of the presence and/or amount of the analyte in the sample. The improvement of the invention comprises using, as the peroxidase, a microperoxidase.

DETAILED DESCRIPTION OF THE INVENTION

The concepts of the present invention reside in an improved assay method for determining the presence of an analyte in a test sample, such as blood serum or plasma, in which an oxidoreductase and a peroxidase, upon contact with the analyte or a derivative thereof in the sample, produces a reaction product which can be determined as a measure of the presence and/or amount of the analyte in the sample. specifically, it has been discovered that in the practice of the method of the invention, a microperoxidase functions similarly to conventionally-used HRPO or other enzymes in typical examples of such assays and, therefore, microperoxidase can be directly substituted for such enzymes which would otherwise be used in such assays, but with the various advantages over the use of such enzymes which are detailed herein.

Microperoxidases are non-enzymatic, catalytic entities which, in accordance with the invention, have been found to provide peroxidative activity in assays such as the aforedescribed. Moreover, when a microperoxidase is used at or near the optimum pH of oxidaoreductase enzymes or reagents used in the assay in conjunction with the microperoxidase (e.g., uricase in uric acid assays) more efficient use of the relatively expensive uricase or other enzymes or reagents can be achieved. In addition, at moderate concentrations, the use of a microperoxidase has been found to provide rapid kinetic responses, and microperoxidases have also been found to be very stable under clinical assay conditions. Moreover, it has been determined that microperoxidases can be readily coupled to antigens, and antibodies, to provide advantageously stable conjugates for use in both heterogeneous and homogeneous immunoassay systems. Microperoxidases, in accordance with the invention, have also been found to provide advantageous performance in non-immunoassay systems wherein peroxidases have conventionally been used.

As is known to those skilled in the art, microperoxidases are fragments of cytochrome C produced by enzymatic cleavage of the protein. Such cleavage leaves small sections of the original cytochroine C amino acid chain with its heme group covalently attached through thioether bonds to the peptide. The structure of compounds characterized as microperoxidases can be generally represented as follows:

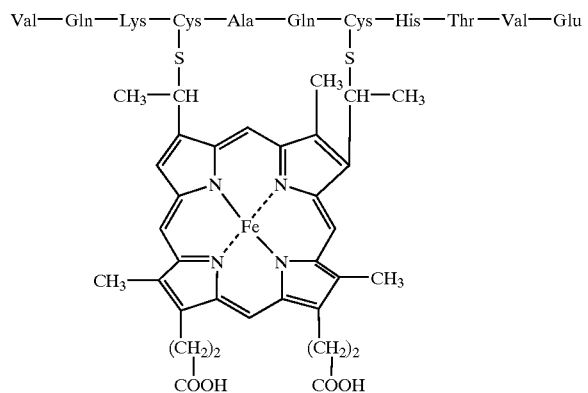

Various microperoxidases are commercially available which are suitable for use in the present invention. For example, the microperoxidase designated MP-8, having a molecular weight of 1502, and microperoxidases MP-9 and MP-11, having molecular weights of 1630 and 1857, respectively, are all suitable and substantially equivalent for use in the invention and are commercially available, for example from Sigma Chemical Company.

Microperoxidases, in accordance with the concepts of the present invention, are particularly well suited for use in place of HRPO in uric acid assays. In a preferred practice of the invention, as set forth in more detail infra, a clinical test sample containing uric acid, usually at concentrations below 12 milligrams per deciliter (mg/dl), is contacted with a mixture of uricase enzyme and microperoxidase in the presence of one or more oxidizable or chromogenic substrates which develop color on oxidation. Such substrates which are useful in the present invention for assay of uric acid as well as other analytes are known in the art, and include, for example, O-phenylenediamine (OPD), 2,2'-azino-di-(3-ethylbenzothiazylene sulfuric acid) (ABTS), 3,3',5,5'-tetramethylbenzidine (TMB), 4-aminoantipyrene (4AAP) and 2-hydroxy-3,5-dichlorobenzene sulfonic acid (DHBS). Such compounds are capable of reaction with peroxides in the presence of microperoxidase to produce a detectable response, such as the development of color on oxidation, as a measure of the peroxide present, and hence as a measure of the uric acid present in the sample. In the practice of the invention, such color development can be conveniently determined in accordance with conventional techniques, and is preferably determined spectrophotometrically using conventional analytical instrumentation, to provide a quantitative measurement of the analyte in the test sample. Alternatively, the color response can, for example, be determined visually, as when it is only desired to use the assay as a semiquantitative screen test for the presence of the analyte.

In addition, luminol or its isomers, for example, can be employed as the substrate for chemiluminescent detection, or various fluorescent compounds such as flourescein or its derivatives can be used as substrates, if desired, to produce a measurable fluorescent response which can be correlated with the presence and/or amount of analyte in a sample under analysis.

In addition to use in the determination of uric acid, it is to be appreciated that a microperoxidase, in accordance with this invention, can also be used as a catalytic unit for the conversion of hydrogen peroxide formed by enzymatic reactions with a number of other compounds, notably including glucose, cholesterol and triglycerides. Thus, those compounds will produce hydrogen peroxide under the action of various known enzymes and reagents, and the hydrogen peroxide so formed can be measured using microperoxidase in a calorimetric or other assay similar to that previously described for uric acid.

In addition, a microperoxidase can, in accordance with the concepts of this invention, be coupled with antibodies to form a conjugate containing the microperoxidase. Exemplary of this technique is a process wherein a sample containing an antigen is contacted with a solid phase such as a polystyrene bead coated with an antibody to the antigen, whereby the antigen becomes immobilized on the bead. After incubation and washing of the bead, a specific antibody to the antigen which has been labeled with microperoxidase is contacted with the bead, incubated, and later washed. The activity of the microperoxidase can then be determined spectrophotometrically or by other means as a measure of the concentration of the antigen in the sample, e.g., through the use of an oxidizable chromogenic substrate, described supra.

A wide variety of antibodies can be coupled with a microperoxidase using homo and hetero bifunctional coupling reagents. Such antibodies include, for example, the monoclonal antibody to Carcino Embryonic Antigen (CEA). In addition, a microperoxidase can also be employed in the instant invention in the labeling of antigens, for example in homogenous immunoassays, and microperoxidases can be employed, using conventional techniques, to label drugs such as theophylline as well as variety of other antibodies and antigens, in accordance with known techniques.

It has also been found, in accordance with the concepts of the present invention, that the sensitivity of an assay utilizing a microperoxidase can be increased by covalently coupling the microperoxidase to polymeric molecules, including for example, dextrans or polyamino acids. Alternatively, the microperoxidase can be coupled with itself. Such conjugates and multiple microperoxidase molecules can then be coupled and used in an assay as previously described.

Having described the basic concepts of the invention, reference is now made to the following Examples, which are provided by way of illustration, but not by way of limitation, of the practice of the invention.

EXAMPLE 1

This Example illustrates the use of microperoxidase as a catalyst in a uric acid assay. A reagent composition is formulated as follows:

| | |
|---|---|
| microperoxidase | 10 milligrams (mg) |
| uricase | 260 international units |
| 4-aminoantipyrine | 270 mg |
| 2-hydroxy-3,5-dichlorobenzene sulfonic acid | 1.33 grams (g) |
| potassium ferrocyanide | 2.1 mg |
| erythromycin | 1 g |
| 0.1M borate buffer (pH 8.2) | 900 milliliters (ml) |

25 ml of glycerol were then added and additional buffer added in an amount sufficient to bring the reagent solution to 1 liter.

A sample of 12.5 microliters (ul) of blood serum was added to 1 ml of the foregoing reagent solution, and the mixture incubated at 37 degrees C. for 5 minutes. Blanks were then prepared by adding 12.5 ul borate buffer to 1 ml of the reagent, and incubating at 37 degrees C. for 5 minutes. After the 5 minute incubation, the absorbance at 515 nanometers (nm) was measured for the blank and that value was subtracted from the absorbance of the sample. The responses for increasing concentrations of uric acid are shown in the following table:

| Uric Acid (mg/l) | Absorbance (at 515 nm) |
|---|---|
| 10 | 0.025 |
| 30 | 0.076 |
| 60 | 0.155 |
| 90 | 0.215 |
| 120 | 0.285 |

It was found that the kinetics of the color development for microperoxidase when used in these assays of the invention were substantially more rapid than those of conventional assays for the same amounts of uric acid, wherein HRPO was employed rather than a microperoxidase. In the assays utilizing a microperoxidase in accordance with the invention, color development reached a maximum in approximately 2–3 minutes, by comparison with 9–10 minutes for similar assays performed not in accordance with the invention but using HRPO in place of the microperoxidase.

In addition, it has been found that when solutions of a microperoxidase and HRPO are added separately at 80 degrees C., the HRPO was totally inactivated within 1 hour, whereas the microperoxidase retained about 90% of its original activity after 3 hours at that temperature.

EXAMPLE 2

This Example illustrates the preparation of microperoxidase-labeled antibodies.

Microperoxidase (11.5 mg) was dissolved in 2 ml of 0.1 M phosphate buffer having a pH of 6.8, and glutaraldehyde was added to make the solution 1.25%. The solution was shaken overnight, the product was chromatographed on Bio-Gel P-2 in 0.15 M NaCl and the brown fractions pooled. The pooled fractions of glutaraldehyde-treated microperoxidase contained microperoxidase at a concentration of 0.718 mg/ml, as measured by absorption spectroscopy at 402 nm.

Monoclonal antibody to Carcino Embryonic Antigen (CEA) (2.11 mg) was dissolved in 3 ml of 50 mM sodium carbonate/bicarbonate buffer having a pH of 9.5. The microperoxidase solution, in an amount of 700 ul, was then added to the antibody solution, and the mixture stirred overnight.

The following morning, 100 ul of a 10% glycine solution were added and stirred for 1 hour. The product was then chromatographed on Sephadex G-50-40 in 0.15 M NaCl. Individual fractions were examined by absorption spectroscopy; the first three brown fractions were pooled and dialysed extensively against a 10 mM phosphate buffer having a pH of 7.0. The ratio of microperoxidase to the antibody was determined to be 4.8.

The labeled antibody was diluted into 10 mM sodium borate and then 10 mM sodium citrate, at a pH of 9.0, and 10-fold dilutions were made. To 100 ul of these dilutions were added 10 ul of 1.3 mM luminol solution. The sample was placed in a photometer capable of measuring the amount of chemiluminescent signal, as represented by signal "counts" (preselected arbitrary units of measure which provide a relative indication of the signal intensity). The signal was initiated by injection of 0.185 M hydrogen peroxide solution into the borate/citrate buffer. The results are shown below:

| (Antibody) | Chemiluminescent Intensity Signal (Counts) |
|---|---|
| 3.23 micrograms/ml | $6.44 \times 10^6$ |
| 32.2 nanograms/ml | $1.30 \times 10^5$ |
| 323 picograms/ml | $6.80 \times 10^4$ |
| 323 picograms/ml | $5.43 \times 10^4$ |
| 0 | $4.02 \times 10^4$ |

EXAMPLE 3

This Example illustrates the preparation and use of microperoxidase-labeled antigens.

A sample of 234 mg of 8-carboxymethyl theophylline and 125 mg of N-hydroxy succinimide (NHS) were suspended in 3 ml of dry dimethylformamide. Dicyclohexylcarbodiimide (227 mg) was dissolved in 5 ml dry dimethylformamide and added to the mixture with stirring. A yellow solution was obtained which became cloudy over 1 hour. The mixture was sonicated for 15 minutes, and the heavy precipitate was filtered off. The solution containing the theophylline NHS-ester was used without purification.

Microperoxidase (1 mg/ml) and an excess of the theophylline NHS-ester were mixed and left at room temperature over the weekend. This material was thereafter diluted with water (5 ml) and purified using high pressure liquid chromatography on a C18 reverse phase column (Magnum 9, 4.6 mm×25 cm), with 0.1% trifluoroacetic acid in water and acetonitrile as the organic modifier as follows: the relative content of acetonitrile was increased from 0% to 25% at the rate of 2.5% per minute. At a flow rate of 1 ml per minute, four peaks were detected at 398 nm; at 18.6 minutes, 22.8 minutes, 24.9 minutes and 30.2 minutes. The 24.9 minute fraction was chosen for its high peroxidative activity and its ability to be inhibited by anti-theophylline sera.

Reagents 1) 0.1 M sodium phosphate buffer, pH 7.4, with 0.01% bovine gamma-globulin (BGG buffer).
2) Theophylline standard solutions. Two-fold serial dilutions of theophylline standard solutions. Two-fold serial dilutions of theophylline in BGG buffer (20 mM to 70 uM).
3) The microperoxidase-theophylline conjugate, prepared as previously described, diluted in BGG buffer.
4) Rabbit antiserum against theophylline, raised by repeated injection of theophylline coupled to bovine serum albumin.
5) Freshly prepared chromogenic substrate solution of 0.01% 3,3',5,5'-tetramethylbenzidine, 0.0044% hydrogen peroxide in 0.1 M sodium acetate and 0.0015 M citric acid, pH 6.0.

The standard solutions of theophylline, in an amount of 50 ul, were incubated with 50 ul of a 215-fold dilution of the antiserum, at room temperature for 30 minutes. 50 ul of a 0.48 micromolar (uM) solution of the microperoxidase-theophylline conjugate were added and incubated for 30 minutes at room temperature. 1 ml of the chromogenic substrate solution was added and the mixture incubated at room temperature for 30 minutes. The reaction was then stopped by addition of 0.25 ml of 2 M sulfuric acid, and the absorbance at 450 nm measured. The results are shown below:

| Theophylline (mM) | Absorbance (450 nm) |
|---|---|
| 20 | 0.135 |
| 10 | 0.123 |
| 5 | 0.180 |
| 2.5 | 0.196 |
| 1.25 | 0.203 |
| 0.265 | 0.235 |
| 0.313 | 0.225 |
| 0.156 | 0.234 |
| 0.078 | 0.233 |
| 0 | 0.196 |

The foregoing data demonstrates that microperoxidase can be used in this type of competition assay for quantitating antigens in fluids, without the need for a separation step. It is to be appreciated that instead of conjugates formed of theophylline and microperoxidase, other antigens can be substituted for the theophylline and used in a comparable way, in accordance with the aforedescribed techniques of the invention.

EXAMPLE 4

This Example illustrates the coupling of microperoxidase to dextran.

Dextran (average molecular weight 40,000 daltons) in an amount of 4 mg, was dissolved in 0.1 ml of 0.05 M sodium carbonate solution, pH 12.0. 10 mg of cyanogen bromide in 5 ul of acetonitrile were added. After 30 minutes on ice, 10 mg of microperoxidase in 0.5 M sodium carbonate, pH 9.5, were added and the mixture incubated overnight. Ethanolamine (30 ul) was then added and the solution stored at room temperature for 2 hours. The sample was then dialysed extensively against a buffer of 0.01 M sodium phosphate and 0.15 M sodium chloride, pH 7.4, before assaying.

EXAMPLE 5

This Example illustrates the preparation of a conjugate of polylysine and microperoxidase.

Microperoxidase (2 mg) and 15 mg of polylysine (average molecular weight 200,000) were dissolved in 0.5 ml of 0.1 M sodium phosphate, pH 7.0. To the above solution was added 0.25ml of a 21 mM glutaraldehyde solution in water, dropwise over 1 hour with gentle shaking. The sample was incubated at room temperature overnight, and then dialysed extensively against PBS.

EXAMPLE 6

This Example illustrates the conjugation of microperoxidase with itself.

Microperoxidase, in an amount of 0.68 mg, was dissolved in 0.1 M phosphate buffer, pH 7.0, containing 0.362 micro moles of glutaraldehyde. The ratio of glutaraldehyde to microperoxidase was 1.04. The reaction was left at 45 degrees C. overnight, whereafter 100 ul of a 1 M solution of glycine in water were added and left at room temperature for 1 hour. The product was chromatographed on Sephacryl S-300, and the peak with an apparent molecular weight of 14,400 was pooled.

EXAMPLE 7

This Example illustrates a comparison of the activities of the microperoxidase conjugates prepared in

EXAMPLES 4–6

The activities of the conjugates of microperoxidase (MP) were tested using chromogenic substrates and hydrogen peroxide, the results being shown in the following table:

| Conjugate Activity | MP/Molecule | Relative Activity |
|---|---|---|
| MP | 1.0 | 1.0 |
| Dextran-MP | 3.9 | 3.9* |
| Polylysine-MP | 2.4 | 2.5* |
| Poly-MP | 7.3 | 2.81** |

*50 ul of the microperoxidase solutions were added to 1 ml of 0.01% TMB and 0.0044% hydrogen peroxide in 0.1M sodium acetate, pH 6.0. After a 30 minute incubation, the reaction was stopped with 0.25 ml of 2M sulfuric acid and the absorbance at 450 nm measured.
**Microperoxidase solutions diluted in PBS at pH 7.5; to 1 ml of the solutions were added 25 ul of a solution containing 0.2M DHBS and 0.54M 4AAP. The reaction was initiated by addition of 10 ul 0.1% hydrogen peroxide solution. The absorbance at 512 nm was monitored.

It can be seen, from the foregoing disclosure, that microperoxidase can be coupled to itself or other molecules such as those aforedescribed and retain all or substantial amounts of its original activity. Thus, coupling thereof to such molecules enables enhanced sensitivity of detection of analytes in enzyme immunoassays and the like, by comparison with conventional techniques wherein horseradish peroxidase or other enzymes are employed.

It will be understood that various changes in the details of procedure, formulations and practice of the invention, as set forth herein, can be made without departing from the spirit and scope of the invention, as defined solely by the following claims.

What is claimed is:

1. A method for determining the amount of uric acid in a sample of biological fluid, said method comprising the step of:
   contacting said sample, at a pH range optimized for the efficient use of uricase, to a reagent solution comprising:
   uricase;
   microperoxidase; and
   a substance capable of producing a detectable response to hydrogen peroxide as a measure of said uric acid present in said sample.

2. A method for determining the amount of uric acid in a sample of biological fluid, said method comprising the steps of:
   contacting said sample with uricase, at a pH range optimized for the efficient use of said uricase, to produce hydrogen peroxide from uric acid contained in said sample;
   subsequently reacting, in the presence of microperoxidase, said uricase-produced hydrogen peroxide with a substance capable of producing a detectable response as a measure of said uric acid present in said sample.

3. A method for determining the amount of uric acid in a sample of biological fluid, said method comprising the step of adding said sample to a reagent solution comprising:
   about 10 mg of microperoxidase;
   about 260 international units of uricase;
   about 270 mg of 4-aminoantipyrine;
   about 1.33 g of 2-hydroxy-3,5-dichlorobenzene sulfonic acid;
   about 2.1 mg of potassium ferrocyanide;
   about 1.0 g of erythromycin;
   about 25 ml of glycerol; and
   from about 900 to about 1000 ml of 0.1 M borate buffer having a pH of about 8.2.

4. The method of claim 1, wherein the substance capable of producing a detectable response is a chromogen.

5. The method of claim 1, wherein the substance capable of producing a detectable response is a chemiluminescent compound.

6. The method of claim 1, wherein the biological fluid is blood serum.

7. The method of claim 1 wherein the substance capable of producing a detectable response is a fluorescent compound.

* * * * *